United States Patent [19]

Liu

[11] Patent Number: 4,655,880
[45] Date of Patent: Apr. 7, 1987

[54] APPARATUS AND METHOD FOR SENSING SPECIES, SUBSTANCES AND SUBSTRATES USING OXIDASE

[75] Inventor: Chung-Chiun Liu, Cleveland Heights, Ohio

[73] Assignee: Case Western Reserve University, Cleveland, Ohio

[21] Appl. No.: 519,071

[22] Filed: Aug. 1, 1983

[51] Int. Cl.$^4$ ............................................. G01N 27/48
[52] U.S. Cl. ........................... 204/1 T; 204/403; 435/817; 436/150
[58] Field of Search ................... 204/1 E, 403; 435/4, 435/11, 14, 25, 26, 288, 291, 817; 436/63, 150

[56] References Cited

U.S. PATENT DOCUMENTS

| | | | |
|---|---|---|---|
| 2,850,359 | 9/1958 | Worthington et al. | 204/1 T |
| 3,260,656 | 7/1966 | Ross, Jr. | 204/403 |
| 3,539,455 | 11/1970 | Clark, Jr. | 204/1 E |
| 3,542,662 | 5/1967 | Hicks et al. | 204/403 |
| 3,623,960 | 11/1971 | Williams | 204/403 |
| 3,707,455 | 12/1972 | Derr et al. | 204/1 E |
| 3,719,564 | 3/1973 | Lilly, Jr. et al. | 204/1 T |
| 3,770,607 | 10/1973 | Williams | 204/403 |
| 3,776,832 | 12/1973 | Oswin et al. | 204/1 T |
| 3,788,950 | 1/1974 | Hicks et al. | 204/1 T |
| 3,838,011 | 9/1974 | Hagen et al. | 204/403 |
| 3,839,154 | 10/1974 | Messing | 435/291 |
| 4,024,042 | 5/1977 | Enfors et al. | 204/403 |
| 4,055,175 | 10/1977 | Clemens et al. | 204/1 T |
| 4,062,750 | 12/1977 | Butler | 204/403 |
| 4,076,596 | 2/1978 | Connery et al. | 204/403 |
| 4,100,048 | 7/1978 | Pompei et al. | 204/195 P |
| 4,172,770 | 10/1979 | Semersky et al. | 204/1 T |
| 4,225,410 | 9/1980 | Pace | 204/1 E |
| 4,260,680 | 4/1981 | Muramatsu et al. | 204/1 E |
| 4,288,544 | 9/1981 | Suzuki et al. | 435/291 |
| 4,324,257 | 4/1982 | Albarda et al. | 128/635 |
| 4,340,448 | 7/1982 | Schiller et al. | 204/1 T |
| 4,364,385 | 12/1982 | Lossef | 128/213 R |
| 4,426,621 | 1/1984 | Galwey et al. | 204/412 |
| 4,450,842 | 5/1984 | Zick et al. | 128/635 |

FOREIGN PATENT DOCUMENTS

| | | | |
|---|---|---|---|
| 1442303 | 7/1976 | United Kingdom | 204/1 E |
| 2073891 | 4/1981 | United Kingdom | |

OTHER PUBLICATIONS

Flato, "The Renaissance in Polarographic and Voltammetric Analysis", Analytical Chemistry Magazine, vol. 44, No. 11, Sep. 1972—pp. 75A–87A.

Copending, commonly assigned U.S. patent application for "Apparatus and Method for Electrochemical Measurements".

Primary Examiner—Terryence Chapman
Attorney, Agent, or Firm—Renner, Otto, Boisselle & Lyon

[57] ABSTRACT

A sensor apparatus is disclosed for sensing substances, species, substrates, etc. using oxidase. The apparatus includes a pair of potentiostat operating electrode systems. In one embodiment each electrode system includes respective working, counter and reference electrodes, and in another embodiment each electrode system includes a respective working electrode and the counter and reference electrodes are shared by both electrode systems. The oxidase material is immobilized on the working electrode of one of the electrode systems. A method also is disclosed for concentration sensing using oxidases.

24 Claims, 12 Drawing Figures

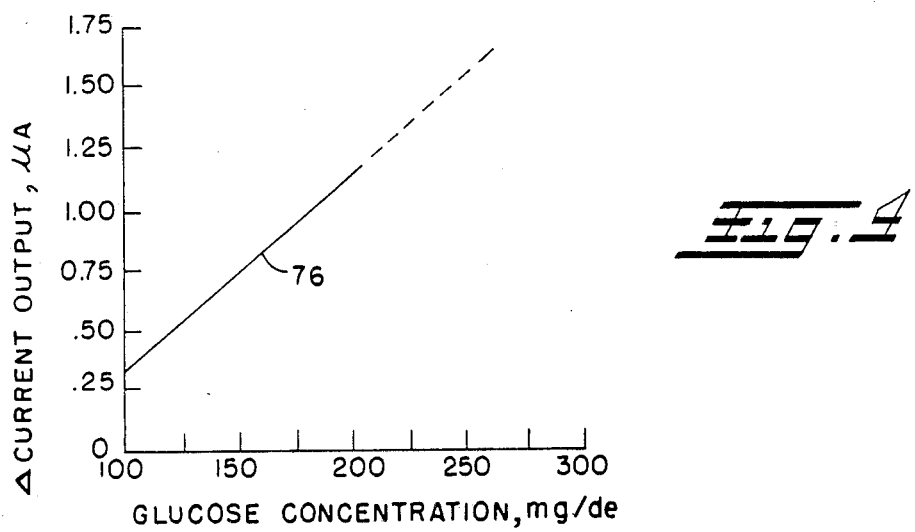
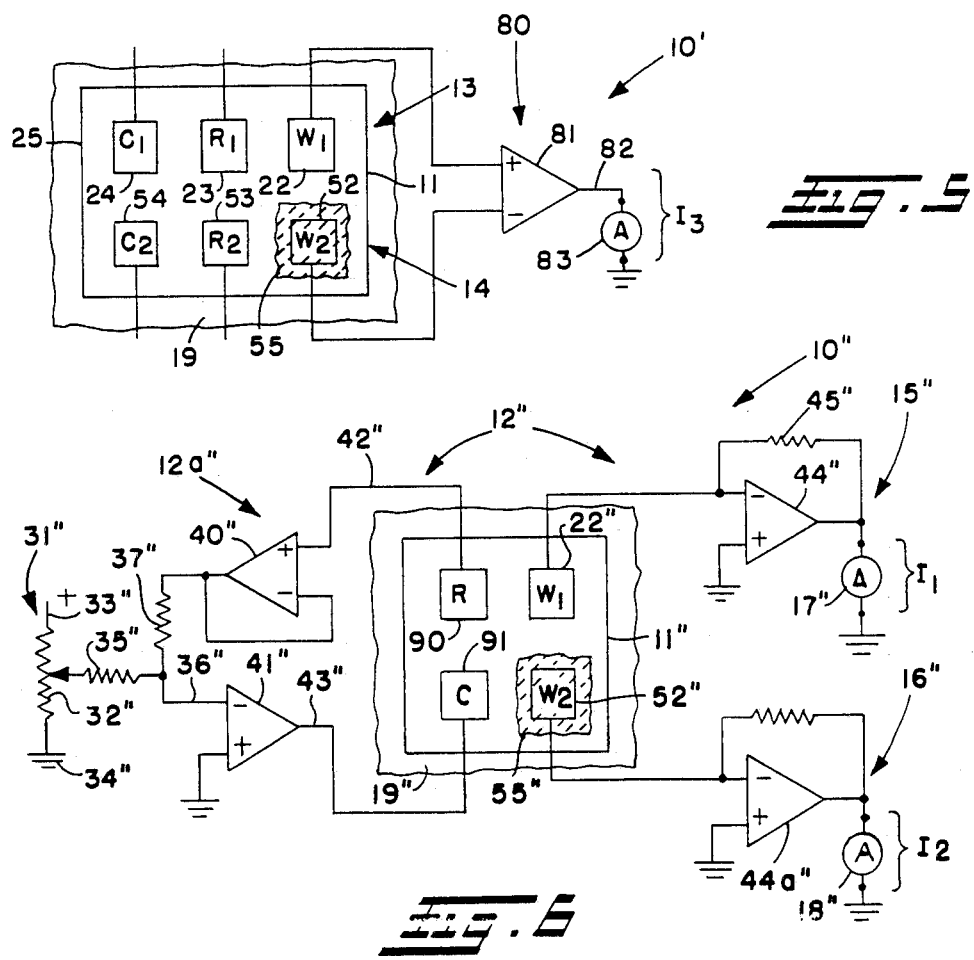

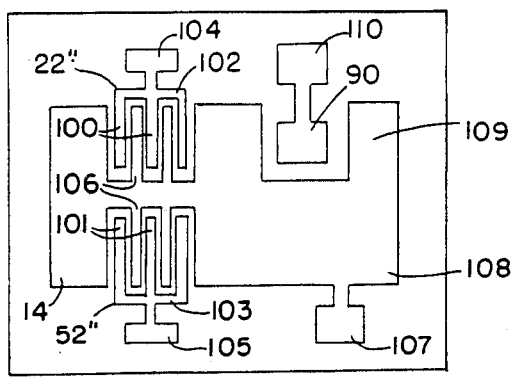
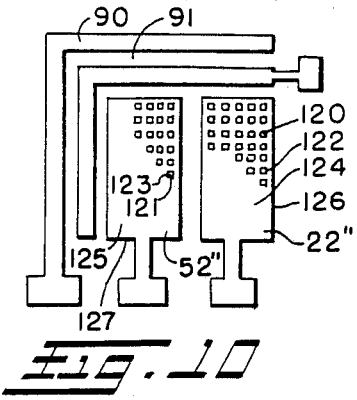
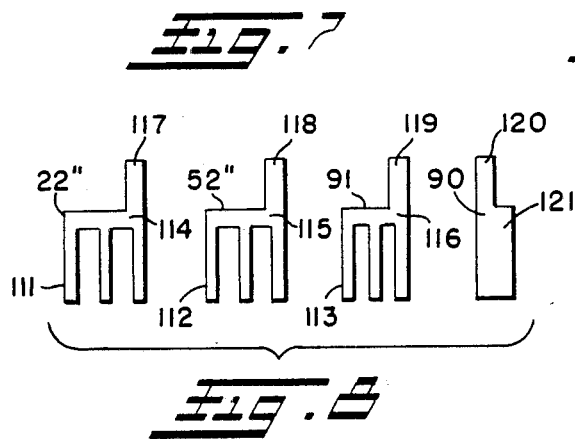
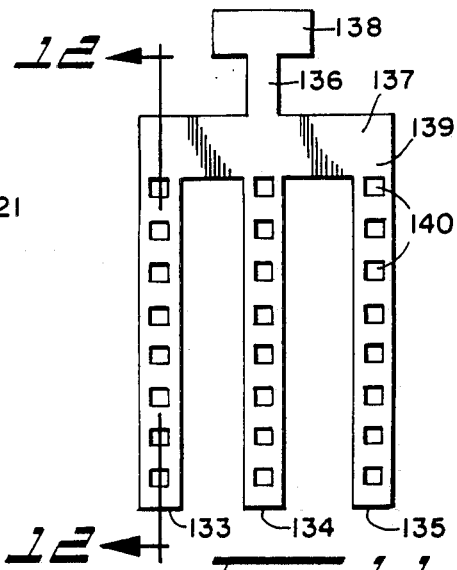
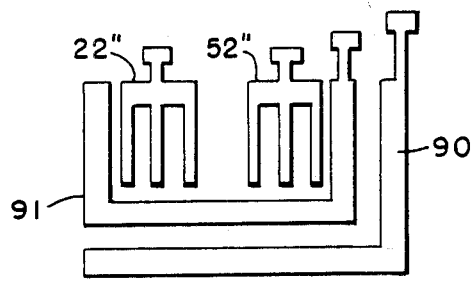
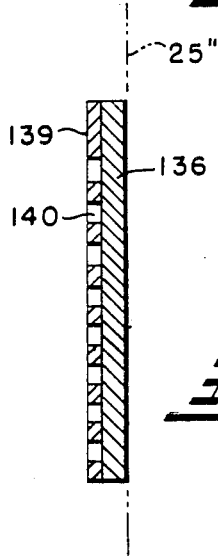

APPARATUS AND METHOD FOR SENSING SPECIES, SUBSTANCES AND SUBSTRATES USING OXIDASE

TECHNICAL FIELD

The present invention relates to electrochemical devices and methods for quantitative or qualitative analyses of a substance in the presence of an enzyme, particularly an oxidase enzyme. Exemplary oxidases are glucose oxidase, lactate oxidase and others, such as those below; and the invention more particularly relates to measuring the glucose, lactate, etc. in the material to be analyzed.

CROSS-REFERENCE TO RELATED U.S. PATENT APPLICATION

Reference is made to copending, commonly assigned, U.S. patent application Ser. No. 407,566, filed August 12, 1982, for "Apparatus and Method for Electrochemical Measurements", the entire disclosure of which hereby is incorporated by reference.

BACKGROUND OF PRIOR ART

Reference also is made to U.S. Pat. Nos. 3,539,455 and 4,340,448, the entire disclosures of which hereby are incorporated by reference. Such patents disclose, for example, approaches to measuring certain materials in the presence of specified enzymes of such materials, for example glucose in the presence of glucose oxidase, etc.

U.S. Pat. No. 3,539,455 discloses a technique for measuring the concentration of glucose by allowing the glucose to diffuse through a membrane into an electrolyte that contains an enzyme, particularly an oxidase, such as glucose oxidase. In the electrolyte a reaction occurs to produce hydrogen peroxide. The electrical current produced during that reaction is measured as a representation of, for example, the glucose concentration. When there is interfering material in the unknown sample, which also contains the glucose, for example, means are provided by the patentee to subtract the current produced by the intefering material from the current produced by the interfering material and that material whose concentration is to be measured. The device of the U.S. Pat. No. 3,539,455 suffers from inaccuracy and instability due to the relatively low signal strength and, as the patentee recognizes, the difficulty in maintaining a uniform oxidase layer at the membrane.

In U.S. Pat. No. 4,340,448 the need for an electrolyte separate from the unknown material, separated therefrom by a selective diffusing membrane, is overcome by immobilizing the enzyme directly on the cathode (working electrode) of the sensor system. The cathode and reference electrode both are inserted into an electrolyte that contains the unknown concentration of material intended for measurement. Such immobilization is achieved by confining the enzyme in a gel that is applied to the working electrode; the gel permits oxygen and glucose to diffuse therethrough.

In the above mentioned application Ser. No. 407,566, there is disclosed an apparatus and method for making electrochemical measurements of certain species, especially of the type that undergo oxidation and/or reduction reactions. The invention disclosed in such application employs a cathode (working electrode), reference electrode, and counter electrode, and these are connected to function in a potentiostat mode. Accordingly, the reactions occurring at the cathode and counter electrode are equal and opposite so that there is no consumption of the electrochemically active species (oxygen, for example), and highly accurate current measurements as a function of the concentration of such species can be made. A particular advantage to such sensor system is the ability to miniaturize the same, including the possibility of placing the three electrodes on a single support that may be placed and used intravivo, while providing improved accuracy and stability by the preferred forms of electrodes and the relatively large signals produced thereby.

As used herein "fluids" includes gases, liquids, vapors, mixtures thereof, and virtually any other material in which an electrochemically active species may occur and/or be detected. In the preferred embodiment and best mode of the invention described below, the electrochemically active species is described as oxygen; however, the electrochemically active species may be other than oxygen. Moreover, although the preferred embodiment and best mode of the invention will be described below with reference to detection of glucose in the presence of glucose oxidase enzyme, it will be appreciated that the principles of the invention may be employed to detect materials other than glucose in the presence of other enzymes.

SUMMARY OF THE INVENTION

Briefly, according to one aspect of the invention, a pair of potentiostat operating electrode systems are provided for sensing of a species in the presence of a corresponding oxidase. Preferably, one measures background oxygen and the other measures oxygen consumption in the presence of the oxidase; and such latter measurement is proportionally representative of the concentration of the unknown material, e.g. glucose. Moreover, such systems are insertable directly into the bath, electrolyte, etc. without any membrane or electrode isolation requirements.

In one embodiment one potentiostat operating electrode system includes three electrodes, namely, working, reference and counter electrodes. The other potentiostat operating electrode system also includes three electrodes, namely, working, reference and counter electrodes, and the oxidase enzyme is immobilized on the working electrode of such other system. The currents measured by the respective electrode systems can be compared, specifically one subtracted from the other, to obtain output information of the glucose concentration as a function of such current comparison.

According to another embodiment of the invention, the two reference electrodes of the respective electrode systems are connected in common, and the two counter electrodes of both electrode systems also are connected in common. The result reduces the overall device to a four electrode system including a pair of working electrodes, one preferably having the enzyme immobilized thereon, a single reference electrode, and a single counter electrode. Circuitry for obtaining information from the electrodes in the four electrode system may be the same or substantially the same as that required for a six electrode system.

According to a further aspect of the invention, there is provided a method for measuring the concentration of an unknown material, such as glucose, which is contained in another medium. According to the method the background concentration of an electrochemically active species is measured by carrying out two equal and opposite reactions in the medium without consuming the species. Moreover, two additional reactions are carried out in the medium, and in one of those the species is consumed due to the presence of an enzyme. Measurements are made of an electrical property related to the first pair of reactions and to the second pair of reactions; and a comparison of the data obtained by such measurements yields information of the concentration of the particular unknown material in the medium. In one embodiment the first pair of measurements is carried out using a three electrode system of working, reference and counter electrodes, and, likewise, the second pair of measurements is carried out using a separate three electrode system, possibly also mounted on the same substrate as the first electrode system is mounted, employing working, reference and counter electrodes.

Important features of the present invention include the stability and accuracy with which the measurements are made and output information is obtained. Using thin film or thick film technique to form the electrodes on a common substrate and immobilizing the enzyme on one of the working electrodes on that substrate contribute to such features of the invention. Moreover, the formation of the electrodes by such thin film or thick film technique enables one or more of the electrodes, particularly the working electrodes, to be formed of multiple portions in a way that substantially increases the reaction surface area and measurable current flow, thus further contributing to such features of the invention.

The foregoing and other objects, advantages and features of the present invention will become more apparent in view of the following detailed description.

BRIEF DESCRIPTION OF THE DRAWINGS

In the annexed drawings:

FIG. 4 is a graphical representation of the measured differential current with respect to glucose concentrations;

FIG. 5 is a schematic illustration of a sensor system according to the invention including a differential amplifier in the output circuit;

FIG. 6 is a schematic illustration of a four electrode sensor system in accordance with the preferred embodiment of the invention;

FIGS. 7-10 are schematic illustrations of several types of electrode configurations in accordance with the invention; and FIGS. 11 and 12, respectively, are plan and partial section views of a preferred electrode configuration.

DESCRIPTION OF PREFERRED EMBODIMENT

Figure 1:
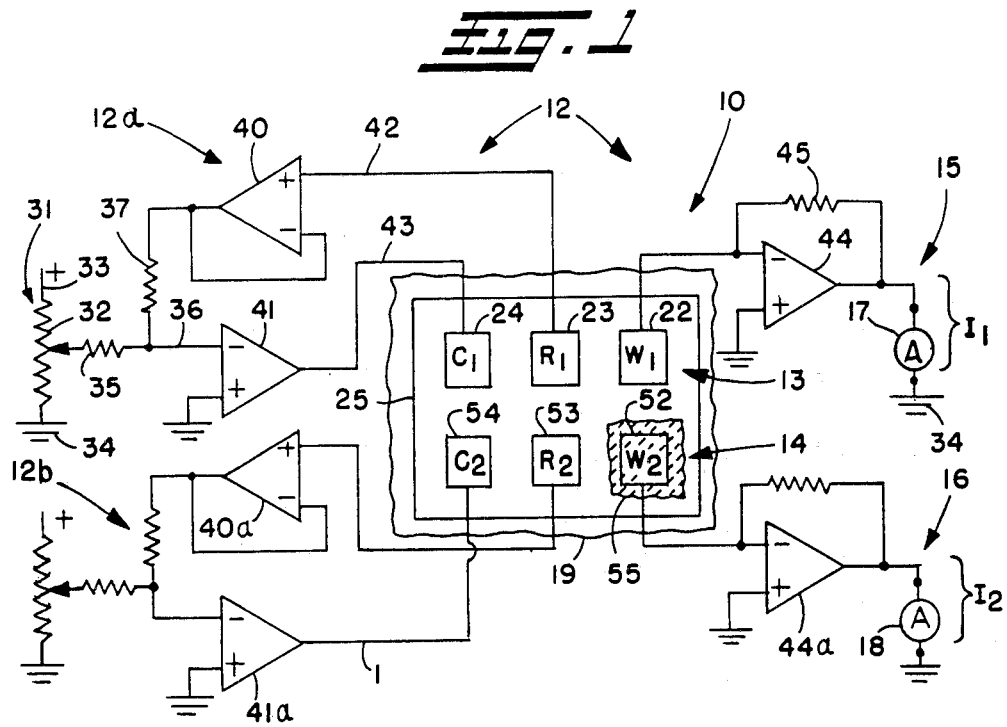
FIG. 1 is a schematic illustration of a sensor system using oxidase in accordance with the present employing two separate three electrode systems and associated circuitry.

Referring in detail to the drawings, wherein like reference numerals designate like parts in the several figures, and initially to FIG. 1, a sensing apparatus using oxidase in accordance with the present invention is generally indicated at 10. The apparatus 10 includes a sensor device 11 and associated electric circuit 12. The sensor device 11 includes two electrode systems 13,14, each of which in association with respective portions 12a,12b of the electric circuit 12 operates in a potentiostat mode to produce at the respective outputs 15, 16 currents $I_1$ and $I_2$ that may be measured and displayed by respective ammeters, more specifically micro ammeters, 17,18. As will be described in greater detail below, the currents $I_1$ and $I_2$ are compared, more specifically the difference between them is obtained, and that difference is proportionally representative of the concentration of the unknown substance, species, substrate, etc. (sometimes used interchangeably herein), according to the preferred embodiment and best mode of the invention glucose, in the sample medium 19 into which the sensor device 11 is placed.

Figure 2:
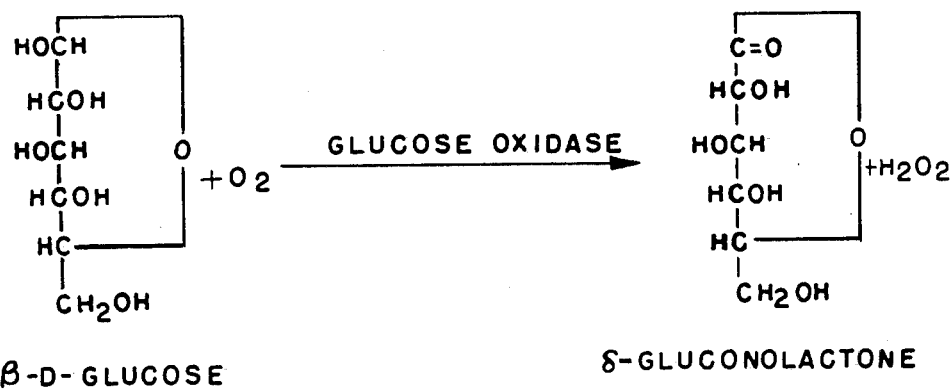
FIG. 2 is a chemical reaction formula representing the chemical reaction occurring at the working electrode on which oxidase is present of the second electrode system in FIG. 1.

The electrode system 13 is intended to measure background level of a particular electrochemically active species, in the preferred embodiment and best mode oxygen, in the sample medium 19, and the electrode system 13, accordingly, functions according to the sensor system disclosed in the above mentioned copending patent application. Thus, the current $I_1$ represents the background concentration of such species (oxygen) and/or interfering material as is mentioned, for example, in U.S. Pat. No. 3,539,455. On the other hand, the electrode system 14 measures current flow due to the chemical reaction illustrated in FIG. 2, for example; more specifically, the electrode system 14 measures current flow as a function of the concentration of the unknown material in the sample medium 19 and the background species (and interfering material) in the presence of the respective oxidase—these being represented by current $I_2$. By subtracting current $I_2$ from current $I_1$, a difference current representing the actual concentration of the unknown substance (glucose) in the sample medium 19 can be obtained, as will be described in greater detail below.

Initially referring to the electrode system 13, the fundamental components thereof include at least three electrodes, specifically a working electrode 22, a reference electrode 23, and a counter electrode 24, preferably all formed by thick film or thin film deposition technique on a common base or substrate 25. The system 13 may be planar, may be comprised of multiple parallel connected electrodes for response speed and accuracy, and may be substantially miniaturized. The electric circuit 12 energizes the system 13 and detects current flow, in the manner to be described in greater detail below.

It is the purpose of the circuit portion 12a, inter alia, to energize the electrodes of the system 13 to maintain a constant voltage between the working electrode 22 and reference electrode 23, even though conductivity of the sample medium, temperature, pH, and/or other parameters may vary. The circuit portion 12a also, preferably in cooperation with the materials of which the electrodes are formed and the electrolyte of the sample medium 19 and species material(s), energizes the system 13 to cause balanced reverse reactions to occur, respectively, at the working electrode 22 and counter electrode 24 and no reaction to occur at the reference electrode 23 when the system 13 is in the electrolyte 19. Such reactions would be, for example, as follows:

At the working electrode is, for example, the following reduction reaction:

$$\tfrac{1}{2}O_2 + H_2O + 2e \rightarrow 2OH^- \tag{1}$$

At the counter electrode is the following oxidation reaction:

$$2OH^- \rightarrow \tfrac{1}{2}O_2 + H_2O + 2e \tag{2}$$

Due to the total reversibility of the reactions occurring at the working 22 and counter 24 electrodes and no reaction occurring at the reference electrode 23, there will be maintained a charge balance in the electrolyte and there will not be any substantial consumption, preferably none at all, of the respective electrodes 22, 23, 24. Moreover, since the reactions are totally reverse of each other, the reaction occurring at the counter electrode does not affect measurement of current flowing at the working electrode 22 as is measured by the meter 17. Since no reaction occurs at the reference electrode 23 and it is in eqilibrium with the electrolyte, the current produced at the working electrode is due only to the oxidation or reduction reaction at the working electrode. Such current is directly proportional to species concentration. Further, since the electrodes are not consumed, prior consumption detrimentally affecting current measurements is eliminated. Accordingly, the system 13 and use thereof in the oxidase sensing apparatus 10 will provide a highly stable accurate measurement of concentration of an electrochemically active species, such as background oxygen and so-called interfering materials, even over long periods of time.

Furthermore, since the reactions occurring at the working and counter electrodes 22, 24 are balanced and reverse, there is no forced reaction; and this together with the non-consumption of the electrodes eliminates the need for the prior large, for example fifty to one, surface area ratio of reference to working electrode convention of the prior art electrochemical sensor technology.

Contributing further to the accuracy and stability of measurements made using a system 13 in the apparatus 10 in accordance with the invention, is the ability to form and actual formation of especially the working electrode 22, and, if desired, the other electrodes, in a multiple parallel connected electrode configuration. Each electrode portion of the working electrode may be quite small so as to have a rapid response; and although each electrode portion is small and, thus, results in only a small current flow contribution, the parallel arrangement of such electrode portions enables the sum of such individual small currents to be measured. Such sum is relatively large and, therefore, results in improved signal-to-noise ratio and, therefore, sensor/measurement accuracy, even in a miniature sensor.

Since a sensor 10 in accordance with the present invention would not require such fifty to one surface area ratio for the working electrode to the reference electrode, it is possible, now, for each of the electrodes 22, 23, 24 to be substantially the same size and, in particular, to be rather small. For example, using available technology relating to thick film and thin film techniques, the electrodes 22, 23, 24 may be deposited on a substrate 25, including polymeric material, that is of a size on the order of about five microns by about five microns. Sizes mentioned herein are surface area sizes for substrates or the like that have, for example, two orthogonal directions, being at least approximately rectangular in shape. Such shape is not essential to the invention, though. The size ranges may be applicable to other shapes of substrates and the like in accordance with the present invention. It is believed that technology is or soon also will be available enabling a system 13 to be made in the so-called micron size range. Without being restricted by the prior fifty to one size requirement for the working electrode to the reference electrode and achieving the relatively high accuracy and stability of the system 13 in the apparatus 10 in accordance with the present invention, such system has substantial utility in biomedical application, including in particular intravivo measurements.

In FIG. 1 the circuit portion 12a of the electrical circuit 12 in apparatus 10 directly associated with the electrode system 13 includes a voltage source 31 formed by an adjustable potentiometer 32 across which the positive and ground terminals 33, 34, respectively, of a DC voltage supply are connected. From the wiper contact of the potentiometer 32 the voltage is coupled by a resistor 35 to line 36 and resistor 37. Operational amplifiers 40, 41, which have appropriate voltage inputs, not shown, are connected, respectively, by lines 42, 43 to the reference electrode 23 and counter electrode 24. The circuit portion 12a also includes a further amplifier 44 with a feedback resistor 45 connected between the working electrode 22 and, via the meter 17, the ground terminal 34. Voltage connections for the amplifier 44 also are provided but are not shown in FIG. 1. It is the purpose of the circuit portion 12a, and particularly of the amplifiers 40, 41, to provide appropriate feedback relation between the reference electrode and voltage source 31, and counter electrode 24 such that as various environmental and/or other parameters may vary in the electrolyte 19, the voltage applied by the source 31 in particular across the working electrode 22 and reference electrode 23 will be maintained constant.

More particularly, the reference electrode 23 is at equilibrium with the electrolyte 19 at the interface therebetween. Amplifier 40 feeds back the potential of the reference electrode 23 to the input of amplifier 41, which, in turn, provides voltage input to the counter electrode. This circuit arrangement, therefore, relies on the reference electrode 23 to set the voltage level. Accordingly, the potential between the reference electrode 23 and working electrode 22 is fixed; and, therefore the potential between the working electrode 22 and the electrolyte is fixed.

Current flow at the working electrode 22, then, may be measured accurately by the meter 17. Such current $I_2$ is due to the reaction occurring at the working electrode 22 and, therefore, represents accurately concentration of the chemically active species, specifically background oxygen in the electrolyte medium 19. The amplifier 44 provides appropriate gain and/or impedance requirements for accurate current measurements. Also, since the meter 17 is connected at one side to a ground reference, the stability of current measurements thereby will be enhanced.

The electrode system 14 also is mounted on the substrate 25 and like the electrode system 13 includes working, reference and counter electrodes 52, 53, 54, for example of the same material, formed in the same way, of the same design, etc. as the electrodes 22, 23, 24. However, in association with the working electrode 52, there is immobilized thereon an enzyme 55. Such an enzyme may be, for example, glucose oxidase contained in a gel in the manner disclosed in U.S. Pat. No.

4,340,448 mentioned above. Moreover, associated with the electrodes 52,53,54, is a circuit portion 12b of the electric circuit 12. The various components and the functionality of those components included in the circuit portion 12b preferably are substantially the same, if not identical, to those included in the circuit portion 12a, and such functionality of the circuit portion 12b with respect to the electrodes 52,53,54 preferably is substantially the same, if not identical, to that of the circuit portion 12a with respect to the electrodes 22,23,24.

However, in operation of the circuit portion 12b in conjunction with the electrode system 14, and especially with the working electrode 52 being in the presence of an enzyme, hereinafter referred to as glucose oxidase, the reactions are different than those occurring in connection with the electrode system 13. More specifically, at the working electrode 52 due to the presence of glucose oxidase the electrochemical reactant, namely oxygen, is consumed according to the reaction, for example, depicted in FIG. 2 of the drawings. Such reaction is a known one. Oxygen ($O_2$) plus glucose in the presence of glucose oxidase 55 at the working electrode 52 results in the production of hydrogen peroxide ($H_2O_2$) and gluconic acid. Such reaction is the same as that disclosed in the above mentioned U.S. Pat. No. 3,539,455. However, in U.S. Pat. No. 3,539,455 hydrogen peroxide must be detected. In contrast, in the present invention, due to the use of the three electrodes 52, 53, 54, the reaction occurring at the counter electrode 54 is still the reverse of that occurring at the working electrode 52.

More particularly, as was described above, the reference electrode 53 is at equilibrium with the electrolyte 19. Amplifier 40a feeds back the potential of the reference electrode 53 to the input of the amplifier 41a, which, in turn, provides voltage input to the counter electrode 54. This circuit arrangement, therefore, relies on the reference electrode 53 to set the voltage level. The potential between the reference electrode 53 and working electrode 52, therefore, is fixed; and, accordingly, the potential between the working electrode 52 and the electrolyte 19 is fixed.

The reactions occurring at the working electrode 52 and at the counter electrode 54, through, unlike those occurring at the working and counter electrodes 22, 24, are not effectively equal and opposite. Rather, at the counter electrode 54 there is an oxidation reaction of the type represented at equation (2) above, and at the working electrode 52, the reaction depicted in FIG. 2 occurs due to the presence of the glucose oxidase enzyme 55. Specifically, glucose and oxygen in the presence of glucose oxidase at the working electrode 52 form gluconic acid and hydrogen peroxide. To support the reaction of FIG. 2, oxygen, i.e. a required active species, is consumed, and a current, which is measurable by the meter 18 as current $I_2$ is produced. The difference between current $I_1$ and current $I_2$ is proportionally representative of the concentration of glucose in the sample medium electrolyte 19 and of the background level of the oxygen, the latter being due to the reaction carried out at the counter electrode 54, for example.

By subtracting current $I_2$ from current $I_1$, then, the effect of the background concentration of oxygen can be eliminated, whereby the difference between such currents is accurately proportionally representative of glucose concentration.

Figure 3:
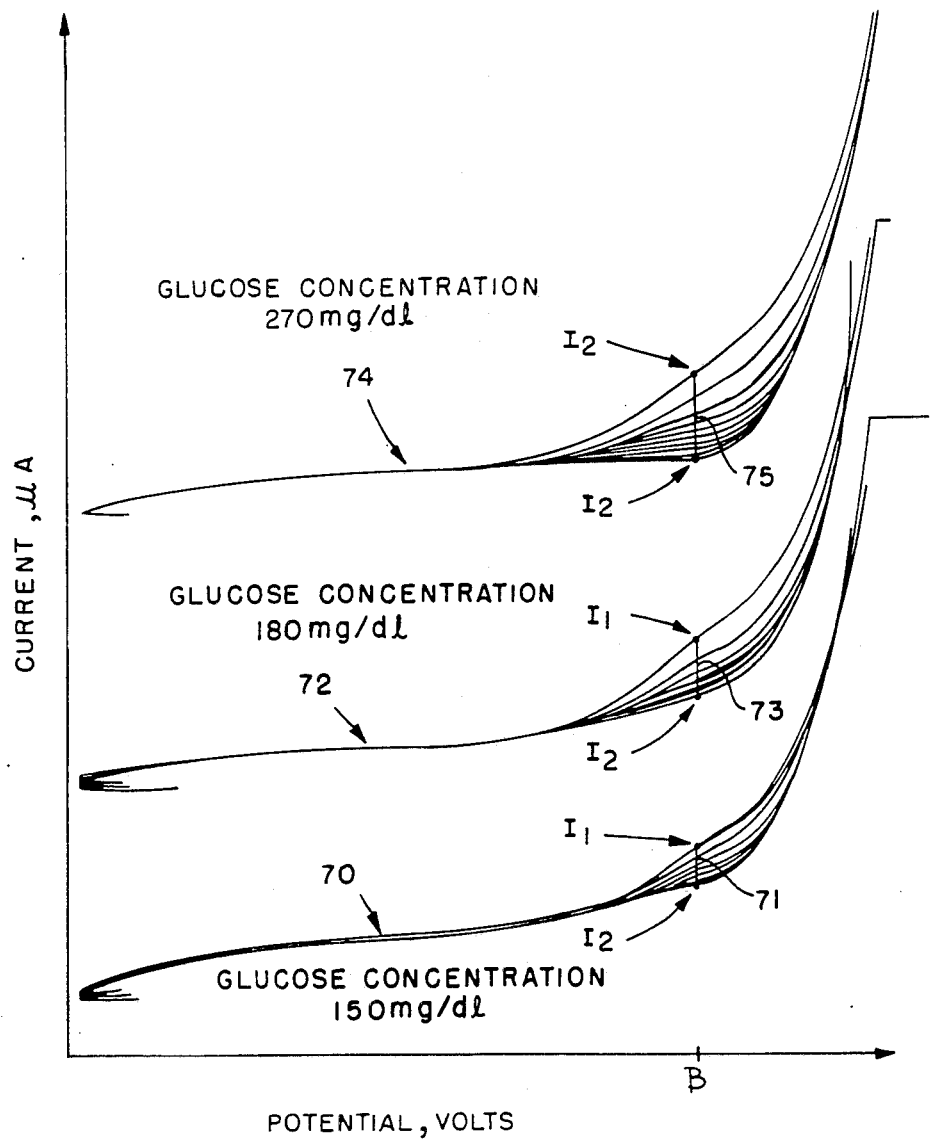
FIG. 3 is a graphical representation of the detected current flow at respective electric potentials and at three different glucose concentrations measured in accordance with the present invention.

Turning briefly to FIG. 3, operation of the sensing apparatus 10 to detect different respective concentrations of glucose in a sample medium containing enzyme 19 is represented graphically. For example, in the group of graph lines 70, the actual glucose concentration was 150 mg. per deciliter. The current level $I_1$ is measured in the absence of glucose oxidase. This current level, $I_1$ thus represents the background oxygen level, and current $I_2$ represents the current level in the presence of the glucose oxidase enzyme 55 after ten minutes of reaction. Thus, the length of the line 71 parallel to the current axis represents the difference between the currents $I_1$ and $I_2$ and, thus, is a proportional representation of glucose concentration, i.e. 150 mg. per deciliter. Similarly, the group of curve lines 72 represents an exemplary use of the invention to detect a glucose concentration of 180 mg. per deciliter of sample medium electrolyte. Associated with lines 72 is the difference line 73 between measured currents $I_1$ and $I_2$, as above, to represent a glucose concentration of 180 mg. per deciliter. The same is true with respect to the curve lines 74 in FIG. 3 and the glucose concentration representation line 75 indicating 270 mg. per deciliter. Thus, it will seen that as the glucose concentration increases, so does the magnitude of the difference lines 71, 73, 75 to obtain a measurable quantified output representation of glucose concentration in the electrolyte 19. The location along the voltage axis of the graph in FIG. 3 at which the current difference measurements are made to obtain the lines 71, 73, 75 may be selected arbitrarily but should be so selected that they provide a measurable current difference, for example at the voltage B illustrated. It will be appreciated, then, that the actual relationship between the magnitude of a current difference, such as line 71, and glucose concentration will be a function of the voltage B at which the measurements are made. The voltage B would be, for example, the voltage provided by the voltage source 31 (FIG. 1) in each of the circuit portions 12a, 12b to the respective electrode systems 13, 14.

In FIG. 4 is a graphical representation of the relationship between the current difference values, e.g. lines 71, 73, 75 of FIG. 3, at a given voltage B with respect to actual glucose concentration in the sample medium electrolyte 19. The graph line 76 in FIG. 4 is a result of actual data measurements and curve fitting. Variations and/or errors due to temperature and/or time of reaction during which glucose loss may occur, for example due to hemoglobin in blood, may distort the curve or graph line 76. In general, though, as is seen in FIG. 4, according to the preferred embodiment and best mode of the present invention, for a given source voltage B, the current difference ($I_1$ minus $I_2$) is directly proportional to glucose concentration.

In FIG. 5 is illustrated a portion of a modified sensing apparatus 10' in accordance with the present invention. In particular, in the apparatus 10' the sensor device 11 and the majority of the circuit portions 30, 60 (the majority of such circuit portions not being shown) are the same as in the apparatus 10 described above with reference to FIG. 1. However, the output 80 for the apparatus 10' is modified from the outputs 15, 16 (FIG. 1) in utilizing a differential amplifier circuit 81 to deliver on line 82 a current to the micro ammeter 83 representing the difference in the currents produced at the respective working electrodes 22, 52. Thus, the current $I_3$ indicated by the ammeter 83 will be proportionally representative of the glucose concentration and avoids the need to make discrete subtractions of currents $I_1$ and $I_2$ in the manner described above. If necessary, the working electrodes 22, 52 may be coupled to the inputs of the differential amplifier 81 via amplifiers 44, 44a (FIG. 1) in order to provide amplified inputs to the differential amplifier 81.

The preferred embodiment and best mode of the present invention is the sensing apparatus 10″ illustrated in FIG. 6. The apparatus 10″ includes a sensor device 11″ and an electrical circuit 12″. In FIG. 6 the double primed reference numbers designate components of the apparatus 10″ which generally correspond in construction and operation to those components designated by like unprimed reference numbers in the apparatus 10 illustrated in FIG. 1.

The sensor device 11″ has two working electrodes 22″, 52″ with glucose oxidase enzyme 55″ immobilized at the working electrode 52″. However, the sensor device 11″ has only a single reference electrode 90 and a single counter electrode 91, and in accordance with the invention, those electrodes 90, 91 perform the same functions and are of the same materials as the pair of reference electrodes 23, 53 and pair of counter electrodes 24, 54, respectively, in the apparatus 10 of FIG. 1. Moreover, the electrical circuit 12″ in the apparatus 10″ requires only, for example, the circuit portion 12a″ together with two respective outputs 15″, 16″. Thus, the circuit portion 12a″ includes, for example, elements 31″ through 37″ and 40″ through 43″, all of which function in the same manner as the corresponding components of the circuit portion 12a described above with reference to FIG. 1. The outputs 15″, 16″ include amplifiers 44″, 44a″, feed back resistor 45″, and the micro ammeters 17″, 18″.

In the apparatus 10″, the ability to utilize only a single reference electrode 90 and a single counter electrode 91 in the sensor device 11″ is possible, it has been discovered, because (a) both reference electrodes 23, 53 (FIG. 1) are maintained at the same reference potential in the electrolyte 19, (b) both counter electrodes 24, 54 (FIG. 1) are maintained at the same voltage with respect to the reference electrodes due to the feed back via the electrical circuit 12 and, in particular, the amplifiers and resistors thereof, (c) the reactions at both counter electrodes 24, 54 (FIG. 1) are the same, and (d) the potential between the respective working electrodes 22, 52 and the corresponding respective reference electrodes 23, 53 (FIG. 1) is fixed and maintained the same.

Operation of the sensing apparatus 10″ will be substantially the same as operation of the apparatus 10 of FIG. 1. More particularly, the reference electrode 90 is at equilibrium with the electrolyte 19″ at the interface therebetween. Amplifier 40″ feeds back the potential of the reference electrode 90 to the input of amplifier 41″, which, in turn, provides voltage input to the counter electrode 91. This circuit arrangement, therefore, relies on the reference electrode 90 to set the voltage level. Accordingly, the potential between the reference electrode 90 and each of the working electrodes 22″, 52″ is fixed; and, therefore, the potential between the respective working electrodes 22″, 52″ and the electrolyte also is fixed.

Current flow at the working electrodes 22″, 52″, then, may be measured accurately by the meters 17″, 18″. The current $I_1$ is due to the reduction of oxygen occurring at the working electrode 22″ and, therefore, represents accurately concentration of the chemically active species, specifically background oxygen in the electrolyte medium 55″. The current $I_2$ is due to the reaction illustrated in FIG. 2 during which oxygen is consumed, and such current $I_2$ represents accurately concentration of the chemically active species and glucose in the electrolyte. The difference between the currents $I_1$ and $I_2$ can be taken manually or automatically in the manners described above. If desired, a differential amplifier may be used in the outputs 15″,16″, for example in the manner illustrated in the apparatus 10′ of FIG. 5 to obtain the difference current $I_3$ representing the glucose concentration in the electrolyte 19.

The small sensor devices 11, 11′, 11″ (hereinafter only the sensor device 11″ will be referred to, it being understood that the comments with respect thereto also are applicable to the sensor devices 11, 11″), especially when employing a flexible polymeric substrate 25″, could be used, for example, by implantation in the body of a person to measure, for example, glucose concentration in the blood or tissue even at the skin, the latter relying on additional techniques of using, for example, conductive gel or polymeric material as an electrolyte at the skin surface.

As an added dimension to the present invention, due importantly to the stability of information obtained from the apparatus 10″, additional transducers/sensors may be employed with the sensor device 11″, including mounting of the same on the substrate 25″, for example. Such additional sensors may be, for example, temperature sensors, pH sensors, conductivity sensors, and so on. Such inclusion may be effected without detrimentally affecting the accurate concentrate information obtained using the apparatus 10″.

Moreover, a sensor device 11″ according to the present invention may be employed as a bare sensor placed in an electrolyte and, just as well, can be used with a selectively permeable membrane in an approach of the type, for example, disclosed in the above mentioned U.S. Pat. No. 3,539,455. The sensor device 11″ also may be used in water containing electrolyte, such as ethylene glycol/water mixture, and, as was mentioned above, even directly in a conductive gel or polymeric type electrolyte.

The substrate 25″ may be formed of plastic, glass, ceramic, alumina, quartz, or any other material that preferably is inert, or at least inert relative to the material of which the electrodes are formed and the material into which the sensor device 11″ is intended to be placed for use. Preferably the substrate is a flexible polymeric material. When used for biomedical purposes, such as to sense glucose concentration, the substrate 25″, indeed the entire apparatus 10″, preferably is disposable. The substrate may be made as small as possible, being of a size adequate to support thereon the required at least four electrodes 22″, 52″, 90, 91 (or six electrodes 22-24, 52-54 of the sensor device 11 in FIG. 1) to function in the manner described herein. Using current thick or thin film technology for applying the electrodes to the substrate, such substrate, and, accordingly, the sensor device 11″ may be small enough, say in the square millimeter size range, to place the same for use on the tip of a medical catheter. In the preferred embodiment, the shape of the substrate 25″ is rectangular, although such shape may be other than rectangular, as is desired. Also, although the substrate 25″ preferably is substantially flat or curved, but nevertheless relatively larger in the two illustrated surface area dimensions/directions than thickness dimension, the substrate and the electrodes may be made in cylindrical or other format, such as the cylindrical format shown in U.S. Pat. No. 4,076,596. The size of the sensor device 11″ may be substantially greater than the square micron or square millimeter size ranges described herein as useful particularly in biomedical applications; for example, for oceanographic, environmental, commercial and/or industrial purposes, the substrate size, and that of the sensor device 11″ as a whole, may be substantially greater, as space and other environmental and/or electrochemical conditions dictate.

Using the thick or thin film technique for applying the electrode material to the substrate 25″, accurately defined electrodes may be formed. Moreover, the size of such electrodes may be quite small and impurities may be minimized due to deposition in a controlled environment.

Preferably the working electrode and the counter electrode are formed of the same material, although this is not a requirement. Such material, though, preferably is inert relative to the substrate and the electrolyte as well as to the electrochemically active species intended to be detected. Thus, such material may be selected from the group of noble metals. A preferred material of which the working electrode is formed may be selected from the group including gold, platinum, silver, and carbon. Likewise, the counter electrode should be of such material. A particular advantage to having a working electrode 22″ and counter electrode 91 formed of the same material is to assure that the reactions occurring there will be substantially totally balanced and reverse of each other and to have the working electrode 52″ also of the same material further avoids an extra difference and possible error source in the apparatus.

Alternatively, the counter electrode(s) may be formed of a material other than that of which the working electrode(s) is (are) formed. For example, the counter electrode(s) may be of silver-silverchloride. Although accuracy and/or stability may be reduced in this case, using the working, reference and counter electrode arrangement according to the present invention, even though the materials of which the counter and working electrodes are formed would be different from each other, that would be a more accurate and stable measurement of concentration than in the prior art, for example because of the accurate maintenance of constant voltage between the working and reference electrodes in the present invention and preferably the minimization, if not exclusion, of reaction at the reference electrode.

The materials of which the reference electrode may be formed, include, for example, silver-silver chloride, mercuric-mercuric chloride (Calomel), and other known, and perhaps unknown, materials. The same is true, too for selecting of the materials for the working electrode and counter electrode; such materials should have the desired inert property electrically conductive property, and/or other properties needed for appropriate operation of the sensor 10.

While a specific preferred enzyme glucose oxidase has been disclosed above, it will be appreciated that other forms of oxidase enzymes may be employed in determining quantitatively concentration of an unknown ingredient, e.g. as glucose, lactate, etc. The invention is readily adapted to be employed with a wide range of oxidase enzymes including one or more of the enzymes set forth in the following group:

| E.C. # | Enzyme |
|---|---|
| 1.15.1.1 | Superoxide dismustase |
| 1.7.3.1 | Nitroethane oxidase |
| 1.4.3.1 | D-aspartate oxidase |
| 1.4.3.3 | D-amino acid oxidase |
| 1.4.3.2 | L-amino acid oxidase |
| 1.4.3.4 | Amine oxidase |
| 1.4.3.5 | Pyridox amine phosphate oxidase |
| 1.4.3.6 | Amine oxidase |
| 1.4.3.7 | D-glutamate oxidase |
| 1.4.3.8 | Ethanolamine oxidase |
| 1.2.3.3 | Pyruvate oxidase |
| 1.2.3.4 | Oxalate oxidase |
| 1.1.3.1 | Glycollate oxidase |
| 1.1.3.4 | Glucose oxidase |
| 1.1.3.5 | Hexose oxidase |
| 1.1.3.6 | Cholesterol oxidase |
| 1.1.3.7 | Aryl alcohol oxidase |
| 1.1.3.8 | L-gulonolactone oxidase |
| 1.1.3.9 | Golactose oxidase |
| 1.1.3.10 | Pyranose oxidase |
| 1.1.3.11 | L-Sorbose oxidase |
| 1.1.3.12 | Pyridoxine 4-oxidase |
| 1.1.3.13 | Alcohol oxidase |
| 1.1.3.15 | L-2-hydroxyacid oxidase |
| 1.3.3.1 | Dehydro-oratate oxidase |
| 1.3.3.2 | Lathosterol oxidase |
| 1.5.3.1 | Sarcosine oxidase |
| 1.5.3.2 | N—Methylamino acid oxidase |
| 1.5.3.4 | $N^6$—Methyl lysine oxidase |
| 1.5.3.5 | 6-hydroxy-L-nicotine oxidase |
| 1.5.3.6 | 6-hydroxy-D-nicotine oxidase |
| 1.8.3.2 | Sulphite oxidase |
| 1.10.3.5 | 3-hydroxyanthranilate oxidase |
| 1.2.3.1 | Aldehyde oxidase |
| 1.2.3.2 | Xanthine oxidase |

One preferred means of immobilizing the enzymes on the working electrode 52″, for example, is through use of a gel which permits oxygen and glucose to diffuse therethrough. One suitable gel is described by G. P. Hicks and S. J. Updike in Analytical Chemistry 38(1966) 726. Another suitable gel is one prepared in the following fashion. The first five of the following six solutions are prepared in 0.1M potassium phosphate buffer at pH 7.3 at room temperature and mixed in the volume shown and the sixth is provided in aqueous suspension.

| | Volume Taken |
|---|---|
| (1) Acrylamide, 500 mg/ML | 0.5 ml |
| (2) Bisacrylamide, 23 mg/ml | 2.0 ml |
| (3) Riboflavin, 0.1 milogram/millimeter | 0.25 ml |
| (4) Ammonium Persulfate, 10 mg/ml | 0.25 ml |
| (5) Glucose Oxidase (110 e.u./mg)(10 mg/ml) | 0.50 ml |
| (6) Catalase (41,397 e.u./mg) | 0.10 ml |
| 6 mg/ml in aqueous suspension | |
| Total | 3.6 ml |

The incorporation of catalase is optional in this invention. The presence or absence of catalase does not alter the signal output produced.

The final solution (3.6 ml) is gassed with 100% nitrogen for seven minutes at about 3–5 bubbles per second as introduced by a Pasteur pipet. The deoxygenated solution is transferred to a sandwich type Plexiglas mold that contains eight (1.5 × 1.5 cm) platinum screens. Each platinum screen is attached with lead wire. After the mold is filled, gel polymerization is initiated by placing the mold within 3 cm of a fifteen watt fluorescent bulb. Polymerization is completed within twenty minutes, at which time the gel coated screens are removed from the mold and stored at 4° C. in 0.1M potassium phosphate buffer until needed.

Although small variations in the amount of acrylamide and bisacrylamide may occur this has little effect on the functioning of the gel. It is desirable to avoid wide variations which could create an unstable gel i.e. too soft or no gel at all.

In using the glucose oxidase and catalase together the amount of each enzyme incorporated into the gel can be varied extensively by holding the amount of one enzyme constant and varying the amount of the other enzyme.

While the gel means are disclosed herein are providing immobilization of the enzyme on the working electrode 52" as a preferred form, it will be appreciated that other forms including covalent coupling, difunctional cross linking, a semi-permeable membrane and adsorption may readily be employed.

In FIG. 7 is shown a preferred embodiment and best mode of the sensor device 11" in accordance with the present invention. In the embodiment in FIG. 7 the substrate 25" is formed of plastic material and is of a size on the order of about one millimeter of about 1.5 millimeters. The working electrodes 22", 52" are of the prong-like fork shape, each having several prongs 100, 101 extending from a common base 102, 103 and a terminal pad 104, 105 connected to the base. The terminal pads provide a place for attaching an electrical lead to the electrode. The counter electrode 91 has a number of fork-like portions 106 that extend in an interdigitated arrangement relative to the prongs 100, 101 of the working electrodes providing the possibility of the several reactions to occur in close proximity in the electrolyte 19" (FIG. 6). The working electrodes 22", 52" and counter electrode 91 are formed of the same material, such as gold, or other material mentioned above, and are applied to the substrate 25" by thick or thin film technique. A terminal pad 107 is connected to the major extent 108 of the counter electrode 14. The reference electrode 90 is located in a U-shape cut out 109 of the counter electrode and has a terminal pad 110 attached thereto. An advantage to the arrangement shown in FIG. 7 is the opportunity for the several reactions to occur at relatively controlled and desired locations somewhat isolated from relatively wide open discontinuities or spaces between respective electrodes.

Turning to FIG. 8, there is shown a side-by-side arrangement of two working, a reference and a counter electrodes 22", 52", 90, 91. The substrate 25" is not shown in FIGS. 8 through 12, which are simply layout drawings of the respective electrodes. In FIG. 8 the electrodes 22", 52", 91 are of the fork-like prong type having prongs 111, 112, 113 extending from the respective common bases 114, 115, 116 and also having terminal pads 117, 118, 119 extending from the respective bases. The reference electrode 90 is sheet or strip-like and has a terminal pad 120 at the end of the strip or sheet portion 121.

In FIG. 9 is a combination of electrode shapes and arrangement. For example, the working electrodes 22", 52" are of the forked prong type surrounded on three sides by a U-shape counter electrode 91. Moreover, the reference electrode 90 is a reverse L-shape surrounding the counter electrode on two sides.

The electrodes also may have a partial circular or arc-shape electrode portion, configuration and arrangement, for example, as is disclosed in the above-mentioned application.

Turning briefly to FIG. 10 there is shown a pair of sheet-like working electrodes 22", 52" that have a plurality of positionally separated electrode portions 120, 121 exposed through openings 122, 123 in an insulation layer 124, 125 on an electrode sheet 126, 127 for increased signal-to-noise ratio while decreasing response time, as was mentioned above. The counter electrode 91 is an inverted L-shape, and so is the reference electrode 90, the former bounding the working electrodes on two sides and the latter bounding the counter electrode on two sides sandwiching the counter electrode between the working and reference electrodes.

In the several embodiments described above it is to be noted that there is no requirement regarding relative positioning of the several electrodes. For example, in several embodiments the counter electrode is adjacent and separates the reference and working electrodes. If desired, though, the reference and working electrodes may be adjacent. Other electrode configurations also may be used. Moreover, there is no showing in FIGS. 7-10 of the immobilized enzyme; however, use thereof in the manner shown for example as 55" in FIG. 6 may be employed.

In FIGS. 11 and 12 is shown a preferred form of working electrode 132 for use in the sensor devices described above. The working electrode 132 has three sheet-like prongs 133, 134, 135, each formed by a thin or thick film process by which a layer of electrically conductive material 136 is deposited on a substrate 25, 25' or 25". A base 137 connects the prongs to each other and to a terminal pad 138. A layer 139 of electrically insulating material is applied over the electrically conductive material 138. Such electrically insulating material has discontinuities therein formed, for example, by an etching process. Such etching process removes selected portions of the insulating material 139 exposing plural discrete working electrode portions 140 and the terminal pad 138.

Since each working electrode portion 140 is relatively small, there will exist a relatively high current density and energy level in proximity thereto helping to induce the desired reduction reaction; the small size and high current density also effect reduction in the time constant for response by the individual working electrode portions 140. Moreover, although the individual currents derived at respective working electrode portions 140 are relatively small, the portions 140 in each prong 133, 134, 135 are connected as in a ladder-like fashion to be in electrical parallel relation. Therefore, the currents are effectively summed in parallel along the respective ladder-like prongs 133, 134, 135, and the currents are further summed at the base 137, as there is current flow with respect to the terminal pad 138. The current sum at the terminal pad, then, is relatively large so as to provide a good signal-to-noise ratio characteristic of the sensor device 11", for example, while the response of the sensor is a relatively rapid one.

Using a sensing apparatus that is made, for example, in the manner described above using thick or thin film technique, the concentration of glucose or other material may be accurately measured. Accordingly, the sensor device would be energized by the electrical circuit to cause reactions at the working and counter electrodes preferably while the voltage between the reference and working electrodes is maintained constant, even though other parameters may vary. The current flowing at the working electrodes may be measured by the meters to obtain information representing concentration.

STATEMENT OF INDUSTRIAL APPLICATION

With the foregoing in mind, it will be appreciated that the invention provides for improvements in electrochemical measurement technology.

What is claimed is:

1. In combination, a pair of potentiostat operating electrode systems for measuring in an electrolyte the concentration of a substance, species or substrate reactive, in the presence of an enzyme, with an electrochemical constituent of the electrolyte, said electrode systems each including a respective working electrode in association with a counter electrode and a reference electrode, and circuit means for energizing said electrodes while maintaining a substantially constant potential between each working electrode and the associated reference electrode with the reference electrode at equilibrium with the electrolyte, the working electrode of one electrode system interfacing not in the presence of said enzyme with the electrolyte, such that the current flowing between the working and counter electrodes of said one electrode system will be functionally related to balanced but reverse reactions between the electrochemical constituent and the electrolyte at such electrodes, and the working electrode of the other electrode system interfacing in the presence of said enzyme with the electrolyte, such that current flowing between the working and counter electrode of said one system is functionally related to an imbalance between such reverse reactions at the working electrode and counter electrode resulting from consumption of electro-chemical constituent by reaction with the substance, species or substrate.

2. The combination of claim 1, wherein said electrochemical constituent is oxygen and said enzyme is an oxidase.

3. The combination of claim 2, further comprising means for locating oxidase with respect to the working electrode of said other electrode system, said oxidase being selected from the group consisting of

| E.C. # | Enzyme |
|---|---|
| 1.15.1.1 | Superoxide dismustase |
| 1.7.3.1 | Nitroethane oxidase |
| 1.4.3.1 | D-aspartate oxidase |
| 1.4.3.3 | D-amino acid oxidase |
| 1.4.3.2 | L-amino acid oxidase |
| 1.4.3.4 | Amine oxidase |
| 1.4.3.5 | Pyridox amine phosphate oxidase |
| 1.4.3.6 | Amine oxidase |
| 1.4.3.7 | D-glutamate oxidase |
| 1.4.3.8 | Ethanolamine oxidase |
| 1.2.3.3 | Pyruvate oxidase |
| 1.2.3.4 | Oxalate oxidase |
| 1.1.3.1 | Glycollate oxidase |
| 1.1.3.4 | Glucose oxidase |
| 1.1.3.5 | Hexose oxidase |
| 1.1.3.6 | Cholesterol oxidase |
| 1.1.3.7 | Aryl alcohol oxidase |
| 1.1.3.8 | L-gulonolactone oxidase |
| 1.1.3.9 | Golactose oxidase |
| 1.1.3.10 | Pyranose oxidase |
| 1.1.3.11 | L-Sorbose oxidase |
| 1.1.3.12 | Pyridoxine 4-oxidase |
| 1.1.3.13 | Alcohol oxidase |
| 1.1.3.15 | L-2-hydroxyacid oxidase |
| 1.3.3.1 | Dehydro-oratate oxidase |
| 1.3.3.2 | Lathosterol oxidase |
| 1.5.3.1 | Sarcosine oxidase |
| 1.5.3.2 | N—Methylamino acid oxidase |

-continued

| E.C. # | Enzyme |
|---|---|
| 1.5.3.4 | $N^6$—Methyl lysine oxidase |
| 1.5.3.5 | 6-hydroxy-L-nicotine oxidase |
| 1.5.3.6 | 6-hydroxy-D-nicotine oxidase |
| 1.8.3.2 | Sulphite oxidase |
| 1.10.3.5 | 3-hydroxyanthranilate oxidase |
| 1.2.3.1 | Aldehyde oxidase |
| 1.2.3.2 | Xanthine oxidase |

4. The combination of claim 2, wherein said electrode systems each includes respective working, reference and counter electrodes separated from the electrodes of the system.

5. The combination of claim 4, further comprising output means for measuring currents flowing between said respective counter electrodes and said respective working electrodes, whereby the difference between the currents is a representation of concentration of the substance, species or substrate in the presence of an oxidase.

6. The combination of claim 5, said circuit means comprising two circuit portions respectively associated with said one and other electrode systems, one circuit portion comprising means for maintaining a constant voltage between said working electrode and reference electrode of said one electrode system, and the other circuit portion comprising means for maintaining the voltage applied across the working electrode and reference electrode of said other electrode system substantially constant.

7. The combination of claim 6, said measuring means comprising a differential amplifier for automatically comparing the magnitudes of the currents to produce an output proportionally representative of the concentration of the substance, species or substrate in the presence of an oxidase.

8. The combination of claim 4, said oxidase comprising an oxidase material contained in a gel immobilized on said working electrode of said other electrode system.

9. The combination of claim 2, wherein both said electrode systems share a single reference electrode and a single counter electrode.

10. The combination of claim 9, further comprising electrically nonconductive support means for commonly supporting all of said electrodes.

11. The combination of claim 9, further comprising output means for measuring currents flowing between said counter electrode and said respective working electrodes, whereby the difference between the currents is a representation of concentration of the substance, species or substrate in the presence of an oxidase.

12. The combination of claim 11, said measuring means comprising a differential amplifier for automatically comparing the magnitudes of the currents to produce an output proportionally representative of concentration of the substance, species or substrate in the presence of an oxidase.

13. The combination of claim 9, said oxidase comprising an oxidase material contained in a gel immobilized on said working electrode of said other electrode system.

14. The combination of claim 1, wherein each of said working electrodes has plural prongs, each of the prongs of a respective working electrode being joined to sum currents therefrom and wherein at least one of said counter and reference electrodes also has prong receiving portions for interdigitated positional relation with respect to the prongs of said working electrodes.

15. The combination of claim 1, wherein each of said working electrodes is sheet-like and has individual electrode portions and comprises a layer of electrically conductive material on an electrically non-conductive substrate, a layer of electrically insulating material on at least a portion of said layer of electrically insulating material to expose individual plural electrode portions.

16. The combination of claim 1, said electrodes comprising electrode material deposited on an electrically non-conductive substrate by thick film or thin film technique.

17. The combination of claim 1, further comprising a substrate of flexible polymeric material, and said electrodes being formed on said substrate by thick film or thin film technique.

18. The combination of claim 17, said substrate being of a size having orthogonal surface area dimensions on the order of from about one micron to ten milimeters by about one micron to ten milimeters.

19. Apparatus for measuring the concentration of a substance, species or substrate in an electrolyte, comprising first and second electrode system means for sensing the substance, specie or substrate, each of said electrode system means comprising a respective working electrode and sharing both a reference electrode and a counter electrode with the other electrode system means; support means for supporting said electrodes; circuit means for energizing said electrodes; output means for measuring currents flowing between said shared counter electrode and said respective working electrodes; and an oxidase material on the working electrode of one of said first and second electrode system means, whereby the difference between the currents is a representation of oxygen consumption as a function of concentration of the substances, specie or substrate.

20. The apparatus of claim 19, said electrodes comprising electrode material deposited on an electrically non-conductive substrate by thick film or thin film technique.

21. The apparatus of claim 19, said support means comprising electrically nonconductive support means for commonly supporting all of said electrodes.

22. The apparatus of claim 19, wherein said oxidase is selected from the group consisting of

| E.C. # | Enzyme |
| --- | --- |
| 1.15.1.1 | Superoxide dismustase |
| 1.7.3.1 | Nitroethane oxidase |
| 1.4.3.1 | D-aspartate oxidase |

-continued

| E.C. # | Enzyme |
| --- | --- |
| 1.4.3.3 | D-amino acid oxidase |
| 1.4.3.2 | L-amino acid oxidase |
| 1.4.3.4 | Amine oxidase |
| 1.4.3.5 | Pyridox amine phosphate oxidase |
| 1.4.3.6 | Amine oxidase |
| 1.4.3.7 | D-glutamate oxidase |
| 1.4.3.8 | Ethanolamine oxidase |
| 1.2.3.3 | Pyruvate oxidase |
| 1.2.3.4 | Oxalate oxidase |
| 1.1.3.1 | Glycollate oxidase |
| 1.1.3.4 | Glucose oxidase |
| 1.1.3.5 | Hexose oxidase |
| 1.1.3.6 | Cholesterol oxidase |
| 1.1.3.7 | Aryl alcohol oxidase |
| 1.1.3.8 | L-gulonolactone oxidase |
| 1.1.3.9 | Golactose oxidase |
| 1.1.3.10 | Pyranose oxidase |
| 1.1.3.11 | L-Sorbose oxidase |
| 1.1.3.12 | Pyridoxine 4-oxidase |
| 1.1.3.13 | Alcohol oxidase |
| 1.1.3.15 | L-2-hydroxyacid oxidase |
| 1.3.3.1 | Dehydro-oratate oxidase |
| 1.3.3.2 | Lathosterol oxidase |
| 1.5.3.1 | Sarcosine oxidase |
| 1.5.3.2 | N—Methylamino acid oxidase |
| 1.5.3.4 | $N^6$—Methyl lysine oxidase |
| 1.5.3.5 | 6-hydroxy-L-nicotine oxidase |
| 1.5.3.6 | 6-hydroxy-D-nicotine oxidase |
| 1.8.3.2 | Sulphite oxidase |
| 1.10.3.5 | 3-hydroxyanthranilate oxidase |
| 1.2.3.1 | Aldehyde oxidase |
| 1.2.3.2 | Xanthine oxidase |

23. The apparatus of claim 22, said oxidase comprising an oxidase material contained in a gel immobilized on said working electrode of said second electrode system means.

24. A method for measuring the concentration of a substance, species or substrate in the presence of a corresponding oxidase, comprising inserting a pair of potentiostat operating electrode systems directly into an electrolyte containing the substrate, species, or substrate of unknown concentration, and while said pair of potentiostat operating electrode systems are in such electrolyte, energizing the electrode systems to produce a first electric current representing the background concentration of an electrochemically active species and a second electric current representative of such background concentration as diminished by the consumption of the electrochemically active species by reaction with the substance, species or substrate in the presence of the oxidase, each of the systems including a respective working electrode, and further comprising immobilizing oxidase material on only one of the working electrodes, and said energizing comprising using plural working electrode portions of each of the working electrodes to induce reactions in proximity thereto and summing the currents developed at the respective working electrode portions.

* * * * *